Figure 5:
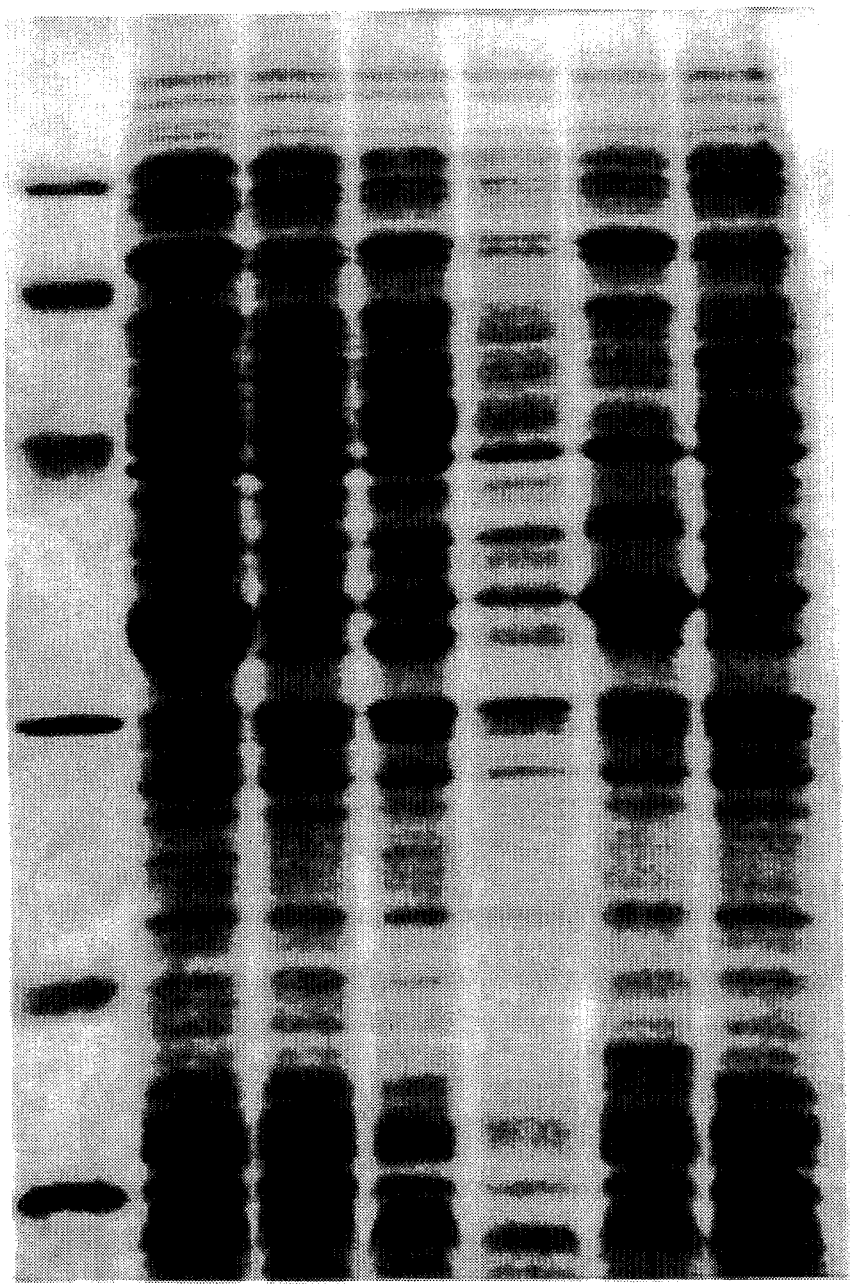

United States Patent [19]
Cuzzoni et al.

[11] Patent Number: 5,525,489
[45] Date of Patent: Jun. 11, 1996

[54] **CLONING OF THE GENE WHICH CODES FOR THE PILINIC SUBUNIT FIM3 OF *BORDETELLA PERTUSSIS***

[75] Inventors: Anna Cuzzoni, Pavia; Barbara Riboli, Cremona; Paola Pedroni, Milan; Francesca De Ferra, San Donato Mil.; Guido Grandi, Segrate, all of Italy

[73] Assignee: Eniricerche S.P.A., Milan, Italy

[21] Appl. No.: 29,952

[22] Filed: Mar. 9, 1993

Related U.S. Application Data

[63] Continuation of Ser. No. 586,069, Sep. 21, 1990, abandoned.

[30] Foreign Application Priority Data

Sep. 22, 1989 [IT] Italy ........................... 21808/89

[51] Int. Cl.⁶ .................... C07H 21/02; C07H 21/04; C12P 21/06; A61K 39/10
[52] U.S. Cl. .................. 536/22.1; 536/23.1; 536/24.32; 424/185.1; 424/184.1; 424/254.1; 435/69.1; 435/69.3; 435/71.1; 435/172.1; 530/350
[58] Field of Search .................... 530/300, 350; 536/27, 22.1, 23.1, 23.7, 24.32; 435/69.1, 69.3, 172.3, 252.3, 320.1, 91.1, 71.2

[56] References Cited

PUBLICATIONS

Livey et al, Molecular Microbiology 1981(2) 203–209 Cloning, & Nucleotide Sequence Analysis of the Serotype 2 Fiberbrad Subunit Gene of *Bordeletta pertussis*.
Suggs et al PNAS 78:6613–6617 1987 Use of Synthetic Oligonucleotides as Hyberdezolion Probes: Isolotosicy Clone cDNA Sequences for human B2–Microglobalin.
Maniatis et al. 1982 Cold Spring Harbor Laboratory Molecular Cloning, a Laboratory Manual see especially Sectors 1, 7, 8, 9, 10, 12.
Cuzzoni et al Nucleic Acids Res 18:1640 Nucleotide Sequence of the fim3 gene from *Bordeletta pertussis* & Homology to fim3 & fimx Gene Products.
de Ferra et al Tokai J. Exp Clin. Med 13:235–237 1988, *Bordetella pertussis* Plin and Pilinteke Genes.
Moo's et al Microbial Pathogenesis 2: 473–484 1981 Characterization of Fimbral Subunits from Bordetella Species.
Livey et al, Molecular Microbiology 1: 203–209 1987 Cloning & Nucleotide Sequence Analysis of the Serotype 2 fimboral Subunit Gene of *Bordeletta pertussis*.
Maniates et al 1982 Cold Spring Harbor, Laboratory of Molecular Cloning, a Laboratory Manual see sections 1, 7, 10, 12.

*Primary Examiner*—Hazel F. Sidberry
*Attorney, Agent, or Firm*—Sughrue, Mion, Zinn, Macpeak & Seas

[57] ABSTRACT

A cloned DNA fragment of *Bordetella pertussis* including the gene which codes for the pilinic subunit fim3, vectors which contain it and microorganisms transformed by the vectors.

The protein and peptides corresponding to at least one epitope of the gene which codes for the pilinic subunit fim3 are particularly useful for the development of acellular anti-pertussis vaccines.

In addition, a strain of Bordetella modified by a recombinant replication or genome-integration vector containing the cloned DNA fragment or the gene or a fraction thereof is particularly suitable for the development of a cellular anti-pertussis vaccine.

9 Claims, 8 Drawing Sheets

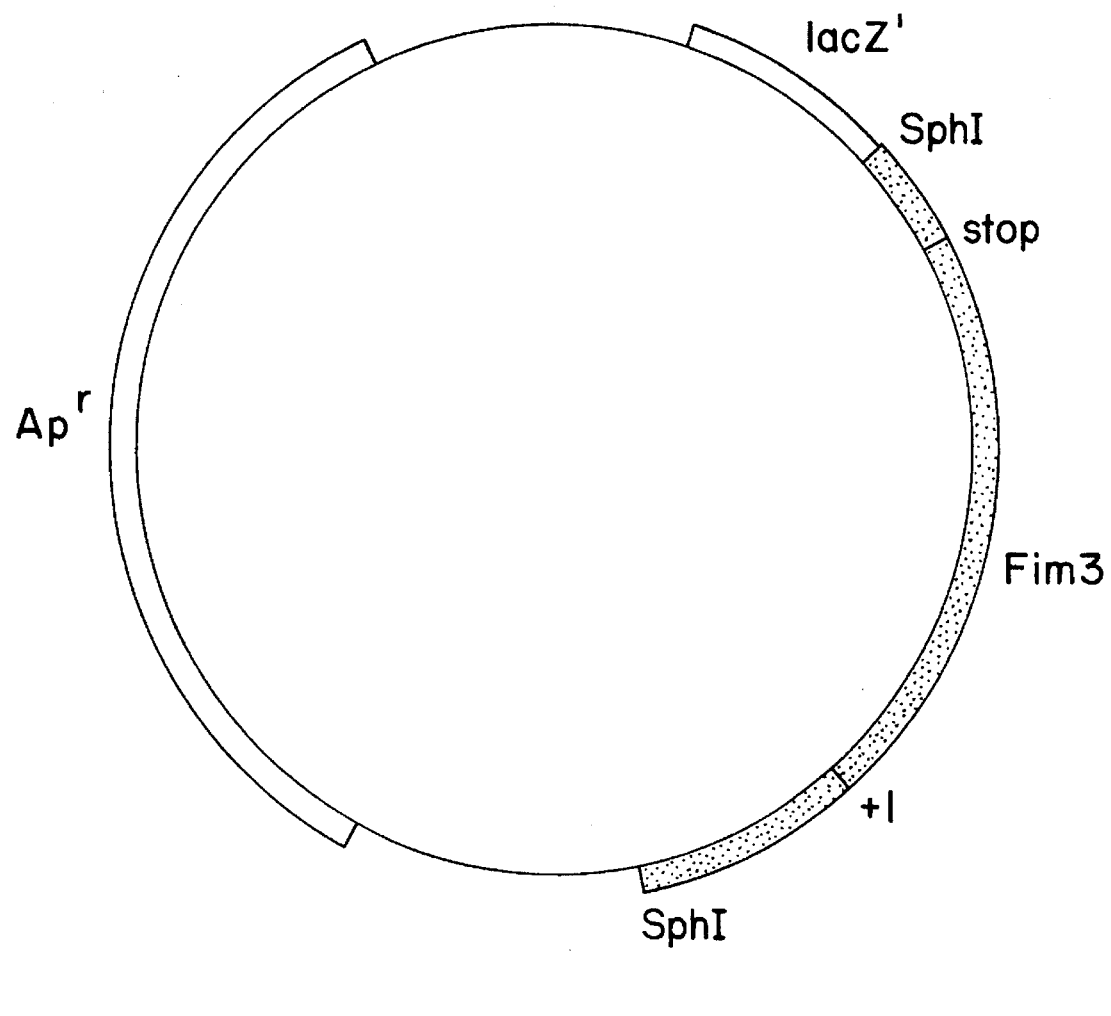

FIGURE 2A

```
ATG TCC AAG TTT TCA TAC CCT GCC CTT GCC GCC CTT ATC CTT GCC
Met Ser Lys Phe Ser Tyr Pro Ala Leu Arg Ala Ala Leu Ile Leu Ala
                        30                                    90

GCC TCG CCC GTA CTG CCA GCG CTG GCC AAC GAC GGC ACC ATC GTC ATC
Ala Ser Pro Val Leu Pro Ala Leu Ala Asn Asp Gly Thr Ile Val Ile
            60                          +1
                                       120
ACC GGC AGC ATC TCC GAC CAG ACC TGC GTC ATC GAA GAG CCC AGC ACC
Thr Gly Ser Ile Ser Asp Gln Thr Cys Val Ile Glu Glu Pro Ser Thr
                                                            180

CTC AAC CAT ATC AAG GTC GTG CAA CTG CCC AAG ATT TCC AAG AAC GCG
Leu Asn His Ile Lys Val Val Gln Leu Pro Lys Ile Ser Lys Asn Ala
        150                                                 240

CTC AGG AAC GAC GGC GAC ACC GCC GGC GAC ACG CCC TTC GAC ATC AAG
Leu Arg Asn Asp Gly Asp Thr Ala Gly Asp Thr Pro Phe Asp Ile Lys
            210
```

FIGURE 2B

```
CTG AAG GAA TGC CCC CTG GGC GCG CTC AAG CTG TAT TTC GAG CCC GGC
Leu Lys Glu Cys Pro Leu Gly Ala Leu Lys Leu Tyr Phe Glu Pro Gly
                        270                            330

ATC ACC ACC AAC TAC GAC ACG GGC GAT CTG ATT GCC TAC AAG CAG ACC
Ile Thr Thr Asn Tyr Asp Thr Gly Asp Leu Ile Ala Tyr Lys Gln Thr
            300                            360

TAC AAC GCA TCC GGC AAC GGC AAC CTG AGC ACC GTG TCG TCC GCC ACC
Tyr Asn Ala Ser Gly Asn Gly Asn Leu Ser Thr Val Ser Ser Ala Thr
                        390                            420

AAG GCC AAG GGC GTG GAG TTC CGC CTG GCC AAC CTC AAC GGC CAG CAC
Lys Ala Lys Gly Val Glu Phe Arg Leu Ala Asn Leu Asn Gly Gln His
                                    450                    480

ATC CGC ATG GGC ACG GAC AAA ACC ACG CAA GCC GCG CAA ACC TTT ACC
Ile Arg Met Gly Thr Asp Lys Thr Thr Gln Ala Ala Gln Thr Phe Thr
```

FIGURE 2C

```
GGC AAG GTC ACC AAT GGC AGC AAG AGC TAC ACC CTG CGC TAT CTC GCC
Gly Lys Val Thr Asn Gly Ser Lys Ser Tyr Thr Leu Arg Tyr Leu Ala
                              510

TCG TAC GTG AAG AAA CCC AAG GAA GAT GTC GAC GCG GCC CAG ATC ACC
Ser Tyr Val Lys Lys Pro Lys Glu Asp Val Asp Ala Ala Gln Ile Thr
            540                                         570

AGC TAC GTC GGC TTT TCC GTC TAC CCC TGA
Ser Tyr Val Gly Phe Ser Val Tyr Pro End
                        600
```

FIGURE 3A

```
+1
Asn Asp Gly Thr Ile Val Ile Thr Gly Ser Ile Ser Asp Gln Thr Cys
                                      10
Val Ile Glu Glu Pro Ser Thr Leu Asn His Ile Lys Val Val Gln Leu
          20                                      30
Pro Lys Ile Ser Lys Asn Ala Leu Arg Asn Asp Gly Asp Thr Ala Gly
                              40
Ala Thr Pro Phe Asp Ile Lys Leu Lys Glu Cys Pro Leu Gly Ala Leu
      50                                      60
Lys Leu Tyr Phe Glu Pro Gly Ile Thr Thr Asn Tyr Asp Thr Gly Asp
                                          70                  80
Leu Ile Ala Tyr Lys Gln Thr Tyr Asn Ala Ser Gly Asn Gly Asn Leu
                                  90
```

FIGURE 3B

```
                          100                        110
Ser Thr Val Ser Ser Ala Thr Lys Ala Lys Gly Val Glu Phe Arg Leu
                                      120
Ala Asn Leu Asn Gly Gln His Ile Arg Met Gly Thr Asp Lys Thr Thr
                          130                        140
Gln Ala Ala Gln Thr Phe Thr Gly Lys Val Thr Asn Gly Ser Lys Ser
                                      150
Ser Tyr Thr Leu Arg Tyr Leu Ala Ser Tyr Val Lys Lys Pro Lys Glu
          160                        170
Asp Val Asp Ala Ala Gln Ile Thr Ser Tyr Val Gly Phe Ser Val Val

Tyr Pro End
```

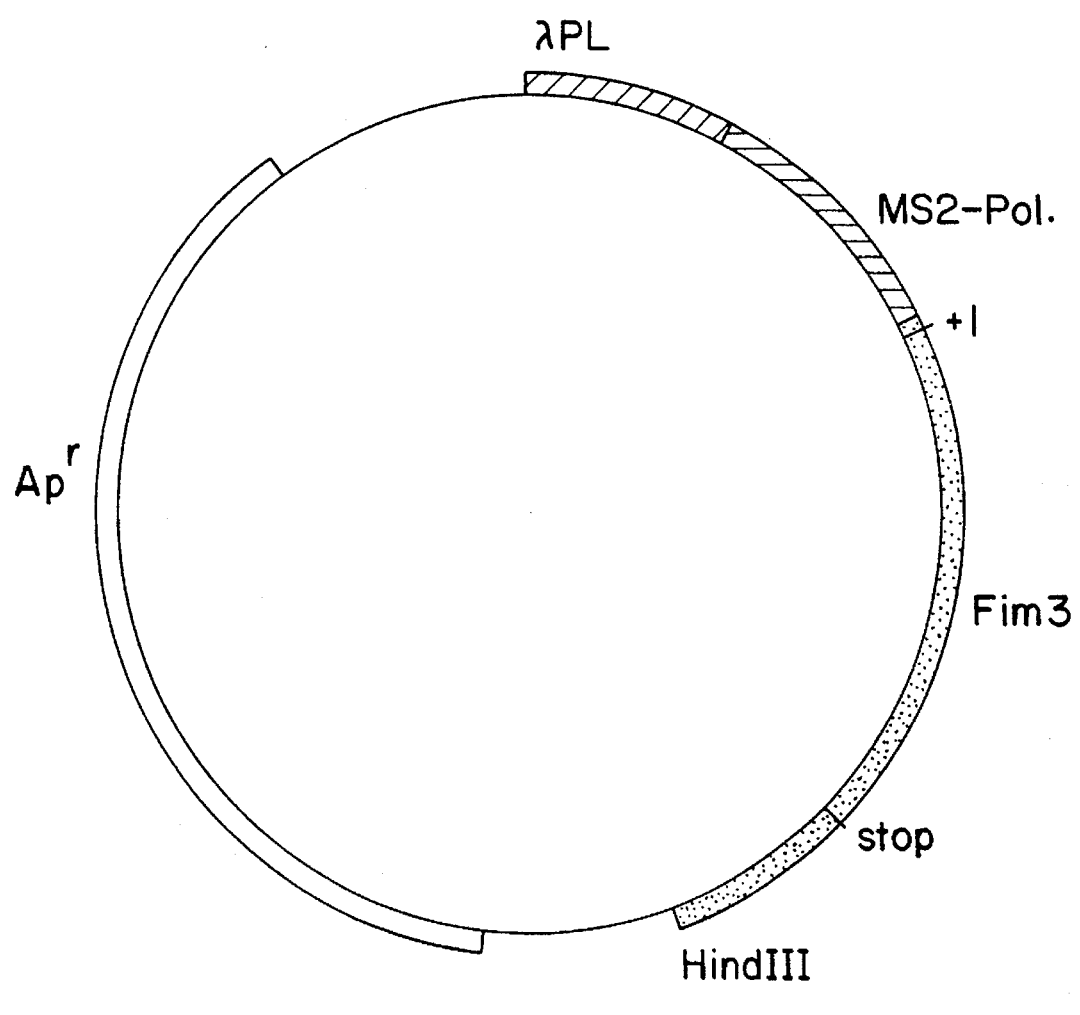

CLONING OF THE GENE WHICH CODES FOR THE PILINIC SUBUNIT FIM3 OF *BORDETELLA PERTUSSIS*

This is a Continuation of application Ser. No. 07/586,069 filed Sep. 21, 1990, now abandoned.

The present invention relates to the cloned and sequenced gene which codes for the pilinic subunit fim3 of *Bordetella pertussis* or a peptide corresponding to at least one epitope thereof, the cloned DNA fragment of *Bordetella pertussis* including the gene, vectors containing it, microorganisms transformed by the vectors and their use for the development of a vaccine effective against pertussis.

Pertussis is a disease of the respiratory tract caused by *Bordetella pertussis* (*B.pertussis*), a microorganism which is transmitted from a sick person to a susceptible healthy individual during the catarrhal and convulsive stage (the virulent stage or Stage I).

Pertussis may cause convulsions, brain damage and sometimes death, particularly in infants and newborn babies without maternal anti-pertussis antibodies; an effective anti-pertussis vaccine is therefore particularly desirable.

Cellular anti-pertussis vaccines are currently used and are constituted by virulent bacteria killed with merthiolate and treated at 56° C. but, whilst they confer permanent protection, they may induce undesirable side effects.

There is therefore a need to develop new anti-pertussis vaccines which do not have the aforesaid disadvantages.

During stage I, *B.pertussis* produces some factors, known as virulence factors, which are necessary for infection to arise and persist.

The pili, for example, are factors involved in the specific adhesion of the bacteria to the cilia of the epithelial cells of the upper respiratory tract, which is an essential stage in the pathogenesis of pertussis since it enables the microorganism to elude the host's defensive system.

The pili or fimbriae are extracellular proteins which are present on the surface of the bacterium and which are constituted by polymerised subunits whose molecular weights can vary from 21000 to 24000 Daltons.

Within the cells, they are expressed as precursors of the protein and are thus constituted by a secretion signal sequence fused to the aminoacid sequence of the mature protein.

The signal sequence is then removed by enzymatic digestion and the protein, suitably processed at the membrane level, is secreted in the mature form (that is without extraneous aminoacid sequences).

Ashworth et al., (1982), (Infect. Immun., 37, 1278–1281) first suggested that the fimbriae of *B.pertussis* were serotype-specific agglutinogens, that is, surface antigens which stimulate the production of antibodies which agglutinate the bacterial cells.

Pilinic proteins of *B.pertussis* were subsequently isolated and purified and were classified as serotype 2 and 3 agglutinogens (Irons et al., (1985), Dev. Biol. Standard, 61, 153–163 ) and fimbriae of serotypes 1, 4, 5, 6 and x have now been identified.

Tests performed on mice inoculated with purified *B.pertussis* pili have shown that these proteins can induce protection against a subsequent intranasal infection with isotypic virulent bacteria.

The development of an acellular vaccine based on the purified pili or on pilinic subunits isolated from the pili must, however, take account of the antigen variations observed in strains of Bordetella.

It has, in fact, been found that immunisation with fimbriae of one particular serotype does not always confer protective immunity against infections caused by a strain containing a different serotype.

Thus, for example, anti-serotype 2 antibodies agglutinate only *B.pertussis* cells containing type 2 agglutinogen and the same applies to anti-serotype 6 antibodies (Cowell, J. L. et al., (1987), Inf. and Immun., 55, No. 4, 916–922).

It has also been observed that, in vitro, anti-serotype 2 and 3 monoclonal antibodies inhibit the bonding of *B.pertussis* to VIRO cells in a serotype-specific manner (Gorringe et al., (1985), FEMS Microbiol. Sett., 26, 5–9).

For these reasons, an anti-pertussis vaccine should contain several immunogenic pilinic subunits.

The genes which code for the pilinic subunits fim2 and fimx have recently been cloned and sequenced (Livey, J. et al., (1987), Mol. Microbiol., 1, (2), 203–209; Pedroni et al., (1988), Mol. Microbiol. 2, 539–543) and the genes have been used for preparing the proteins by recombinant DNA techniques, giving high yields.

As regards the subunit fim3, Mooi et al., (Microb. Pathog., (1987), 2, 473–484) have described part of the aminoacid sequence of the mature protein.

The characterisation of the gene which codes for this subunit, in terms of nucleotides and aminoacids, is now described for the first time.

A subject of the present invention is therefore the cloned and sequenced gene which codes for the pilinic subunit fim3 of *Bordetella pertussis* or a peptide including at least one epitope thereof.

Another subject of the present invention is a cloned DNA fragment of *Bordetella pertussis* which includes the gene which codes for the pilinic subunit fim3 or for nucleotide regions corresponding to at least one epitope of that sequence.

A further subject of the present invention is a cloning vector with expression in host cells and including the DNA fragment.

Another subject of the present invention is a cloning vector with expression which includes the gene which codes for the pilinic subunit fim3 of *Bordetella pertussis* or for a peptide including at least one epitope thereof, in which the gene is placed under the control of regulating sequences recognised by the host.

Another subject of the present invention is a host microorganism transformed by the vectors and capable of expressing the protein fim3 or peptides corresponding to at least one epitope thereof.

Another subject of the present invention is the use of the microorganism for the preparation of a cellular or an acellular anti-pertussis vaccine.

Further subjects of the present invention are the immunogenic pilinic protein fim3 characterised by the aminoacid sequence of FIG. 3 and peptides corresponding to at least one epitope thereof.

A further subject of the present invention is a therapeutically effective composition which can confer protective immunity against infections caused by strains of *Bordetella pertussis* and which contains an immunogenically effective quantity of a transformed microorganism or of a peptide as defined above.

Further subjects of the present invention will become clear from a reading of the following description and experimental examples.

The term cloned relates to a DNA sequence which has been inserted in a heterologous host cell with the use of a vector which enables its replication. The term epitope means an antigenic determinant of an immunogenic molecule which includes a molecular configuration which can induce a protective immune response in a mammal when presented in a suitable form.

The term synthetic peptide means a peptide which does not occur naturally as such and which is produced by chemical synthesis by known techniques (in this connection, see the synthesis, method described by Merrifield et al., (1983), J. Am. Chem. Soc., 105, 6442) or by recombinant DNA methods.

The gene according to the present invention, which codes for the expression and secretion of the pilinic subunit fim3 of *Bordetella pertussis,* is characterised by the nucleotide sequence given in FIG. 2 (SEQ. ID. No. 3).

This gene can be produced by the preparation of a gene library representative of the genome of *B.pertussis* and the subsequent selection of the DNA fragments with specific probes.

In practice, a culture of *Borderella pertussis* was grown in a suitable medium and lysed, and the DNA was extracted and purified by conventional techniques and partially digested with a restriction enzyme. The fragments resulting from the enzymatic digestion were then ligated to a cloning vector previously digested with suitable restriction enzymes and the reaction mixture was used to transform competent host cells by techniques known in the recombinant DNA field.

The positive clones, that is, those containing the cloning vector including a heterologous DNA fragment, were then selected on suitable culture media and analysed by the Northern blot or Southern blot hybridisation techniques with the use of radioactively marked probes.

According to one embodiment of the present invention, a gene library of *B.pertussis* was constructed by the partial digestion of its DNA with the restriction enzyme Sau 3A and the subsequent isolation and cloning of the fragments with molecular weights of about 35–45 kilobases (kb) in a cosmid with expression in *E.coli.*

The positive clones, selected on a suitable culture medium such as, for example, LB with added ampicillin, were then analysed with the aid of a pair of probes produced by the synthesis and subsequent marking of oligonucleotides corresponding to largely preserved regions of the aminoterminal sequences of fim3 or fim2. In particular, the oligonucleotides according to the present invention have the following nucleotide sequences (SEQ. ID. No. 1 and 2):
Probe A: 5'CCTTCAGCTTGATGAT 3'
Probe B: 5'GTGATGACGATGGTG 3'

The oligonucleotides were marked at the 5'OH by means, for example, of the technique described by Arrand, J. E., "Nucleic Acid Hybridization: A practical approach", Ed. B. D. Hames & S. Higging, Press Washington DC, p. 34, 1985).

Some clones which hybridised with both of the probes were identified by the method described above. These clones contained an 850-bp DNA fragment which was then sequenced by subcloning in a pUC vector or in an M13 phage by known techniques.

More particlularly, the DNA fragment was subcloned in the vector pUC 18 and the resulting hybrid plasmid (pSM 306) was sequenced by the method of Sanger et al., (1977), (PNAS, 74, 5463) with the aid of the successive primers strategy described by Strauss et al., (1986), (Anal. Biochemo, 154, 553). The sequencing reactions were carried out by the standard Boehringer method on plasmids denatured with the use of a "pUC Sequencing" kit.

The DNA fragment contained a single open-reading frame (gene) of 609 bp which codes for the precursor of the pilinic subunit fim3. More particularly, the gene was constituted by the nucleotide sequence which codes for the signal peptide (25 aminoacids) for the secretion of fim3 fused to the sequence ( structural gene) which codes for the mature pilinic subunit fim3 ( 177 aminoacids) (FIG. 2, SEQ. ID. No. 3).

According to one aspect of the present invention, the cloned DNA fragment containing the fim3 gene can be introduced into a vector for expression in host cells selected from bacteriophages, cosraids or replication or genome integration plasmids available either commercially or from authorised collection centres. The recombinant vectors produced are then used to transform host cells selected from the group consisting of bacteria, yeasts and higher eukaryotic cells.

According to one embodiment of the present invention, a plasmid for genome integration in Bordetella can be used to conjugate Bordetella strains which cannot produce the pilinic subunit fim3 and which are selected from the group consisting of *B.pertussis, B.parapertussis* and *B.bronchiseptica.*

According to a further aspect of the present invention, the gene which codes for the pilinic subunit fim3 or a peptide including at least one epitope thereof can be introduced into a cloning vector for expression in host cells and the recombinant vector thus produced is used to transform a host organism.

The gene according to the present invention, or a fragment thereof, can be fused to the region which codes for the aminoterminal sequence of a gene of the vector transcribed and translated by the host organism and possibly including the control sequences associated therewith.

Alternatively, the gene which codes for the pilinic subunit fim3 or peptides corresponding to at least one epitope thereof can be expressed by the insertion of the gene in the correct reading frame, immediately after the ATG site which starts translation, so that the gene inserted replaces the coding sequence which is normally transcribed and translated by the bacterial control region. This control region includes a promotor and the ribosomal recognition site. The DNA coding sequence which is to be expressed can be positioned correctly with the aid of suitable restriction enzymes and, if appropriate, with the use of a suitable synthetic oligonucleotide linker. A control sequence for terminating the transcription and translation can be inserted in the correct reading frame downstream of the cloned gene. The DNA insert may be the entire sequence which codes for the subunit fim3 and its secretion signal sequence or a nucleotide fragment thereof which codes for the mature protein fim3 or an epitope of that protein.

Nucleotide fragments suitable for the purpose can be prepared by the digestion of a suitable clone with restriction enzymes and, if necessary, by the subsequent treatment of one or both terminals with Bal 31 so as to remove some of the DNA in a controlled manner. Controlled digestion is achieved by the appropriate selection of the buffer, the temperature, the duration of the reaction and the quantity of enzyme used.

The controlled expression of a DNA fragment according to the present invention can be achieved with the use of the 5' and 3' terminal regions of the coding sequence or other known regions containing the promotor regulating elements and enhancers.

Vectors suitable for the purposes of the present invention may be selected from those known in the art and useful for the cloning of the DNA sequence and its expression in a host microorganism.

According to one embodiment of the present invention, the structural gene which codes for the mature protein fim3, that is, without the region which codes for the fim3 secretion signal sequence, was cloned in the plasmid pEX 34C (Nicosia et al., (1987), Infect. Immun., 55, 963–967) which contains the "left" promotor/operator of the lambda phage of E.coli and the gene which codes for the DNA polymerase of the MS2 phage, producing the recombinant plasmid pSM 364.

This vector is very useful since it contains a strong promotor and can be induced by temperature variation when inserted in the E.coli strain K12, Δhl, Δtrp (Remault et al., 1981), Gene, 15, 81–93) which carries the modified cI lambda gene integrated in the chromosome.

According to the present invention, analysis of the total protein content extracted from cultures of E.coli transformed with pSM 364 grown under induction conditions (42° C.) and under repression conditions (28° C.) showed that a protein with a molecular weight corresponding to that of the pilinic subunit fim3 and the 98 aminoacid sequence of MS1 polymerase was present only in the induced cultures.

This indicated that the pilinic subunit fim3 was expressed correctly.

The scope of the present invention therefore includes a fused protein constituted by a portion of a protein of the host strain, such as the N-terminal sequence, and the mature subunit fim3, or at least an epitope of the subunit fim3, such as the C-terminal sequence. The present invention also relates to the pilinic subunit fim3 or peptides including at least an epitope thereof, when they are produced by one of the methods of the present invention.

Like the Bordetella strains modified at genome level by the DNA fragment or the fim3 gene according to the present invention, these products can be incorporated in a vaccine for conferring immunity against pertussis.

For this purpose, the immunogenic products may be presented in association with a pharmaceutically acceptable carrier. The antigen products can be used alone or in combination with other B.pertussis immunogens.

Pharmaceutically acceptable carriers are liquid media suitable as vehicles for the introduction of the antigen material according to the present invention into a patient. An example of such a carrier is a saline solution. The pilinic subunit fim3 or a peptide thereof or a fused protein may be present in the carrier in soluble form or in suspension and may be made soluble by the addition of a pharmaceutically acceptable detergent.

The vaccine may also include an adjuvant for stimulating the immune response and thus increasing its effectiveness. A suitable adjuvant may be, for example, aluminium hydroxide.

Conveniently, the vaccine is formulated so as to contain an immunogenically effective quantity of the subunit fim3 or a peptide thereof or of a modified strain of Bordetella.

One or more doses of the vaccine, suitably formulated, may be administered in order to induce immunity against pertussis in mammals.

The vaccine according to the present invention may be administered by conventional techniques including parenteral and oral introduction. The treatment may consist of a single dose of the vaccine or several doses over a certain period of time.

BRIEF DESCRIPTION OF THE APPENDED DRAWINGS

FIG. 1: shows the restriction map of the plasmid pSM 306.

FIG. 2: shows the nucleotide sequence (SEQ. ID.No.3) of the gene which codes fop the pilinic subunit fim3 of Bordetella pertussis. The region underlined indicates its secretion signal sequence and +1 indicates the first aminoacid residue of the mature protein.

FIG. 3: shows the aminoacid sequence (SEQ. ID. No. 4) of the mature pilinic protein fim3 deduced from its nucleotide sequence.

FIG. 4: shows the restriction map of the recombinant vector pSM 364.

FIG. 5: shows acrylamide gel in denaturing conditions with SDS stained with Coomassie blue:

1 and 2: total protein content extracted from an E.coli strain which expresses the protein fim2 fused to the first 98 aminoacids of MS2 polymerase grown under induction conditions (42° C.) and at 28° C. respectively;

3 and 4: total protein content extracted from an E.coli strain containing the recombinant plasmid pSM 364 grown under induction conditions (42° C.) and at 28° C. respectively;

5 and 6: total protein content extracted from an E.coli strain which expresses the protein fimx fused to the first 98 aminoacids of MS2 polymerase grown under induction conditions (42° C.) and at 28° C. respectively.

According to the present invention, the plasmid pSM 306 has been deposited as E.coli JM101 (pSM 306) at the American Type Culture Center under the reference ATCC 68067.

The following experimental examples are illustrative of the invention and are not limiting.

EXAMPLE 1

Extraction of the Chromosomal DNA From B.pertussis SA1

100 ml of fermentation broth having the following composition:

| Beta casamino acids (Difco) | 14 g |
| --- | --- |
| KCl | 0.2 g |
| MgCl$_2$.6H$_2$O | 0.1 g |
| K$_2$PO$_4$ | 0.5 g |
| nicotinic acid | 0.02 g |
| glutathione | 0.01 g |
| starch | 1.00 g |
| H$_2$O | 1 l |
| pH 6.8 | | previously sterilised at 120° C. for 15 minutes were inoculated with the B.pertussis strain SA1 and kept under agitation (200 revolutions per minute, rpm) at 37° C. for 3 days.

At the end of this period, the cells were separated from the supernatant liquid by centrifuging in a Sorvall RC-5B model SS 34 rotor at 4° C. at 5000 rpm for 10 minutes and then washed (2×120 ml) with a solution containing 100 mM NaCl, and 50 mM Tris-HCl, pH 7.5.

The resulting suspension was centrifuged again as described above and the cells were recovered and resuspended in 10 ml of a buffer solution (100 nM EDTA, 50 mM NaCl, 2.5% sucrose, pH 6.9) containing 1 mg/ml of lysozyme (SIGMA).

The suspension was kept under gentle agitation at 37° C. for 30 minutes, SDS (sodium dodecyl sulphate) was then added to give a final concentration of 1% and the mixture was kept at 60° C. for 30 minutes.

1 mg/ml of proteinase K previously incubated at 37° C. for 30 minutes in 1×SSC (1×SCC=0.15M NaCl, 15 mM sodium citrate) was then added to the solution and the resulting mixture was left to react at 37° C. for 2 hours.

After NaCl had been added to give a final concentration of 1M, the mixture was kept in ice for 30 minutes and then centrifuged. The DNA in the supernatant liquid was precipitated with 2–3 volumes of cold ethanol (−20° C.), collected with a glass rod and resuspended in 10 ml of 0.1×SSC. The suspension was kept at ambient temperature (20°–25° C.) under gentle agitation for one night and, after the addition of RNAse (10 gamma/ml), at 37° C. for 30 minutes.

The saline concentration of the solution was then brought to 1×SSC, the solution was extracted with phenol (1 volume) and the DNA precipitated by the addition of isopropanol dropwise to the solution which was kept at ambient temperature under gentle agitation. The DNA was then recovered by centrifuging and resuspended in 1 ml of 0.01×SSC.

The quantity of chromosomal DNA, evaluated by a spectrophotometric reading taken at OD 260 with the use of a Perkin-Elmer spectrophotometer, Mod. 515, was 0.645 mg/ml.

EXAMPLE 2

Cloning of the Gene Fim3

A) Construction of a genome bank of *B.pertussis* SA1 in Sau 3A.

In order to obtain the sequence of the gene fim3, a genome bank of *B.pertussis* SA1 was constructed with the use of the cosmid pHC 79.

500 μg of the chromosomal DNA extracted as described in Example 1 were partially digested with 5 units of Sau 3A (BRL) in a buffer mixture at 37° C. for 15 minutes.

The DNA thus digested was precipitated by the addition of an equal volume of ethanol to the solution, separated by centrifuging at 4° C. for 15 minutes at 12000 rpm in an Eppendorf centrifuge and then resuspended in 500 μl of TE buffer (10 mM Tris-HCl, pH 8.00, 1 mM EDTA).

The solution was loaded on to a gradient comprising from 10% to 40% of sucrose dissolved in 35 ml of a buffer containing 1 mM NaCl, 10 mM Tris-HCl, pH 7.5, and 1 mM EDTA. The gradient was then centrifuged at 26,000 rpm for 16 hours in a Beckman SW28 rotor and fractions of 1 ml each were then collected. The molecular weight of the DNA contained in each fraction was determined by electrophoresis on agarose (Maniatis et al., "Molecular Cloning: A practical laboratory manual", Cold Spring Harbor, New York, 1982). The fractions containing DNA fragments of 35–45 kb were then dialysed, the DNA was precipitated with ethanol as described above and then separated by centrifuging and resuspended in 10 mM Tris-HCl, pH 7.5, 1 mM EDTA buffer at a concentration of 1 μg/ml. The chromosomal DNA fragments were then cloned in the cosmid pHC 79.

In practice, 20 μg of the cosmid were digested with 40 units of the restriction enzyme BamHI (BRL) at 37° C. for 1 hour in 200 μl of buffer mixture. 2 μg of chromosomal DNA were ligated with 0.5 μg of cosmid DNA in 10 μl of ligation mixture in the presence of 1 unit of T4 DNA ligase at 14° C. for one night.

At the end of this time 2.5 μl of the ligation mixture were used in vitro with Stratagene's Packagene Kit. The recombinant cosmids thus obtained were used to infect the *E.coli* strain JM101 (BRL) and the transformants were selected on LB agar medium (DIFCO). 15,000 positive colonies were selected.

B) Screening of the gene library in Sau 3A

Approximately 1500 of the colonies were analysed by hybridisation with the following pair of probes (SEQ.ID. No. 1 and 2):
Probe A: CCTTCAGCTTGATGAT and
Probe B: GTGATGACGATGGTG
which are homologous with the largely preserved N-terminal regions between the genes fim2 and fim3.

The oligonucleotides were synthesised with the use of Beckmann's automatic One Plus System and then marked at the 5'OH end with $10^5$ μCi of gamma ($P^{32}$) ATP as follows:

200 ng of each oligonucleotide were suspended in 30 μl of an aqueous solution constituted by 3 μl of kinase buffer (Boehringer), 21 μl ATP, 10 units per ml of T4 polynucleotide kinase 10 (1 μl).

The mixture was kept at 37° C. for 45 minutes and then at 65° C. for 10 minutes to de-activate the enzyme.

The marked probes were purified on Sephadex G-50 columns in TE buffer, pH 8.00, to remove the marker which had not been incorporated. 13 fractions, each of 150 μl, were collected and 2 μl of each fraction were put in 4 ml of scintillating liquid and measured in a scintillator.

The positive colonies of the bank in cosmids were transferred on to nitrocellulose filters (Schleicher & Schull, 0.45 μm) and, after lysis with NaOH, their DNA was immobilised by the Southern blot technique (Maniatis et al., 1982). The filters were hybridised with the probes A and B in parallel. The pre-hybridisation treatment was carried out at 65° C. for 6 hours whilst the hybridisation was effected at 41° C. for the probe A and at 45° C. for the probe B for one night.

The filters were then washed at 25° C. with 0.1% sodium dodecyl sulphate (SDS), 6×SSC for 1 hour and placed in contact with Kodak 5 X-Omat AR radiographic plates. 5 clones which hybridised with both probes were isolated by the method described above.

One of the cosmids extracted from the clones contained an SpHI fragment with 850 bp whose nucleotide sequence was different from that of the gene fim2.

EXAMPLE 3

Subcloning of the SpHI Fragment with 850 bp in pUC 18

1 μg of the plasmid pUC 18 (Boehringer) was digested in 10 μl of digestion buffer with 5 units of SpHI retriction enzyme at 37° C. for 1 hour.

The enzymatic reaction was stopped at 65° C. for 10 minutes and the DNA precipitated with ethanol and separated by centrifuging.

60 ng of the plasmid DNA were then ligated with 60 ng of the 850 bp SpHI fragment in 20 μl of ligation mixture in the presence of 1 unit of T4 DNA ligase at 14° C. for one night. The ligation mixture was then used to transform competent *E.coli* JM101 cells. The transformants were then selected on plates of LB agar medium to which 50 μg/ml of ampicillin, 40 μg/ml of X-gal and 125 μg/ml of IPTG had been added, at 37° C. for 18 hours.

The plasmids extracted from some of the positive clones thus obtained contained the 850-bp SpHI fragment. One of these plasmids, designated pSM 306, (FIG. 1) was further characterised.

EXAMPLE 4

Sequencing of pSM 306

The plasmid pSM 306 was sequenced by the method of Sanger et al., (1977), (PNAS, 74, 5463) with the aid of the successive primers strategy described by Strauss et al., (1986), (Analyt. Biochem. 154, 353). The sequencing reactions were carried out on the denatured plasmids by the standard Boehringer method with the use of a "pUC Sequencing" kit, with alpha (P$^{32}$) dATP as the tracer and the Macrophor sequencing system (LKB) for the electrophoretic separation.

The 850-bp fragment contained the 609-bp gene fim3 which codes for the precursor of the pilinic subunit fim3. More particularly, the gene was constituted by the nucleotide sequence which codes for the signal peptide (25 aminoacids) for the secretion of fim3 fused to the sequence (structural gene) which codes for the mature pilinic subunit fim3 (177 aminoacids) (FIG. 2, SEQ. ID. No. 3).

EXAMPLE 5

Expression of the Pilinic Subunit fim3 in *E.coli*

A) Construction of the recombinant plasmid pSM 364.

10 µg of the plasmid pSM 306 were first digested with 10 units of Hind III (BRL) at 37° C. for 1 hour and were then treated with 10 units of BalI at 25° C. for 1 hour.

A 660-bp BalI—Hind III fragment with two cytosine residues at the BalI blunt end followed by the triplet which codes for the first aminoacid (Asn) of the mature protein fim3 and a Hind-III site situated 120 nucleotides downstream of the TGA stop triplet was then separated from the digestion mixture on 8% agarose gel.

In parallel, 100 ng of the vector pEX 34C were digested with 0.1 units of EcoRI at 37° C. for 1 hour in digestion mixture.

Its ends were then blunted by incubation with 0.25 units of the Klenow fragment of DNA polymerase in the presence of 0.025 mM dATP and dTTP at 30° C. for 15 minutes. Finally, the vector was digested with 1 unit of Hind III at 37° C. for 1 hour and, after the enzyme had been de-activated at 65° C. for 10 minutes, the DNA was separated and ligated with 67 ng of the 660-bp fragment containing the gene fim3. The reaction was carried out in 50 µl of ligation mixture in the presence of 1 unit of T4 DNA ligase at 23° C. for one night.

The ligation mixture was then used to transform competent *E.coli* K12, Δ Hl, Δtrp cells and the transformants were selected on LB agar medium with the addition of 50 µg/ml of ampicillin at 28° C. for one night. From the positive clones obtained, one was isolated which contained the expected recombinant plasmid, designated pSM 364, whose restriction map is shown in FIG. 4. p0 B) Analysis of the proteins expressed by *E.coli* (pSM 364)

*E.coli* K12, ΔHl, Δtrp cells transformed by the recombinant plasmid pSM 364 were grown in duplicate in 20 ml of LB medium with the addition of 50 µg/ml of ampicillin at 28° C. for one night. After the cultures had been diluted to OD 1.0 at 600 fim, one flask was brought to 42° C. for 1 hour (induction) whilst the other was kept at 28° C. also for 1 hour (repression). 500 µl of each culture were then treated as described by Hirst et al., (1984), (J. Bacteriol., 157, 637–642) in order to extract the total protein content.

The proteins were analysed under discontinuous, denaturing conditions by means of 12.5% acrylamide gel. Subsequent staining with Coomassie blue revealed a band of approximately 31,000 Daltons amongst those extracted from the induced culture. This band corresponded to the fused heterologous protein of 31,692 Daltons constituted by 101 aminoacids (11,514 Daltons) (98 aminoacids of MS2 polymerase and 3 of the polylinker) and 177 aminoacids (20178 Daltons) of the mature protein fim3 (FIG. 5).

This band was also displayed by reaction with anti-MS2 polymerase polyclonal antibodies (Sclavo) in a Western blot test carried out by the method of Towbin et al., (1979), (PNAS, 76, 4350–4354).

SEQUENCE LISTING

SEQUENCE TYPE: Nucleotide
SEQUENCE LENGTH: 16 base pairs
STRANDEDNESS: Single
TOPOLOGY: Linear
MOLECULE TYPE: Synthetic
PROPERTIES: DNA probe

CCTTCAGCCT GATGAT

\*\*\* \*\* \*\*\*

SEQ ID NO: 2
SEQUENCE TYPE: Nucleotide
SEQUENCE LENGHT: 15 base pairs
STRANDEDNESS: Single
TOPOLOGY: Linear
MOLECULE TYPE: Synthetic
PROPERTIES: DNA probe

GTGATGACGA TGGTG

SEQ ID NO: 3
SEQUENCE TYPE: Nucleotide with corresponding protein
SEQUENCE LENGTH: 609 base pairs
STRANDEDNESS: Single
TOPOLOGY: Linear
MOLECULE TYPE: Genomic DNA
FEATURES: from 1 to 75 bp leader sequence;
 from 76 to 606 mature peptide
PROPERTIES: fim3 pilinic subunit gene

| ATG | TCC | AAG | TTT | TCA | TAC | CCT | GCC | TTG | CGC | GCC | GCG | CTT | ATC | CTT | GCC |
|-----|-----|-----|-----|-----|-----|-----|-----|-----|-----|-----|-----|-----|-----|-----|-----|
| Met | Ser | Lys | Phe | Ser | Tyr | Pro | Ala | Leu | Arg | Ala | Ala | Leu | Ile | Leu | Ala |

48

| | | | | | | | | | | | | | | | | |
|---|---|---|---|---|---|---|---|---|---|---|---|---|---|---|---|---|
| GCC | TCG | CCC | GTA | CTG | CCA | GCG | CTG | GCC | AAC | GAC | GGC | ACC | ATC | GTC | ATC | |
| Ala | Ser | Pro | Val | Leu | Pro | Ala | Leu | Ala | Asp | Asp | Gly | Thr | Ile | Val | Ile | 96 |
| ACC | GGC | AGC | ATC | TCC | GAC | CAG | ACC | TGC | GTC | ATC | GAA | GAG | CCC | AGC | ACC | |
| Thr | Gly | Ser | Ile | Ser | Asp | Gln | Thr | Cys | Val | Ile | Glu | Glu | Pro | Ser | Thr | 144 |
| CTC | AAC | CAT | ATC | AAG | GTC | GTG | CAA | CTG | CCC | AAG | ATT | TCC | AAG | AAC | GCG | |
| Leu | Asp | His | Ile | Lys | Val | Val | Gln | Leu | Pro | Lys | Ile | Ser | Lys | Asp | Ala | 192 |
| CTC | AGG | AAC | GAC | GGC | GAC | ACC | GCC | GGC | GCC | ACG | CCC | TTC | GAC | ATC | AAG | |
| Leu | Arg | Asn | Asp | Gly | Asp | Thr | Ala | Gly | Ala | Thr | Pro | Phe | Asp | Ile | Lys | 240 |
| CTG | AAG | GAA | TGC | CCC | CTG | GGC | GCG | CTC | AAG | CTG | TAT | TTC | GAG | CCC | GGC | |
| Leu | Lys | Glu | Cys | Pro | Leu | Gly | Ala | Leu | Lys | Leu | Tyr | Phe | Glu | Pro | Gly | 288 |
| ATC | ACC | ACC | AAC | TAC | GAC | AGC | GGC | GAT | CTG | ATT | GCC | TAC | AAG | CAG | ACC | |
| Ile | Thr | Thr | Asn | Tyr | Asp | Ser | Gly | Asp | Leu | Ile | Ala | Tyr | Lys | Gln | Thr | 336 |
| TAC | AAC | GCA | TCC | GGC | AAC | GGC | AAC | CTG | AGC | ACC | GTG | TCG | TCC | GCC | ACC | |
| Tyr | Asn | Ala | Ser | Gly | Asn | Gly | Asn | Leu | Ser | Thr | Val | Ser | Ser | Ala | Thr | 384 |
| AAG | GCC | AAG | GGC | GTG | GAG | TTC | CGC | CTG | GCC | AAC | CTC | AAC | GGC | CAG | CAC | |
| Lys | Ala | Lys | Gly | Val | Glu | Phe | Arg | Leu | Ala | Asn | Leu | Asp | Gly | Gln | His | 432 |
| ATC | CGC | ATG | GGC | ACG | GAC | AAA | ACC | ACG | CAA | GCC | GCG | CAA | ACC | TTT | ACC | |
| Ile | Arg | Met | Gly | Thr | Asp | Lys | Thr | Thr | Gln | Ala | Ala | Gln | Thr | Phe | Thr | 480 |
| GGC | AAG | GTC | ACC | AAT | GGC | AGC | AAG | AGC | TAC | ACC | CTG | CGC | TAT | CTC | GCC | |
| Gly | Lys | Val | Thr | Asp | Gly | Ser | Lys | Ser | Tyr | Thr | Leu | Arg | Tyr | Leu | Ala | 528 |
| TCG | TAC | GTG | AAG | AAA | CCC | AAG | GAA | GAT | GTC | GAC | GCG | GCC | CAG | ATC | ACC | |
| Ser | Tyr | Val | Lys | Lys | Pro | Lys | Glu | Asp | Val | Asp | Ala | Ala | Gln | Ile | Thr | 576 |
| AGC | TAC | GTC | GGC | TTT | TCC | GTC | GTC | TAC | CCC | TGA | | | | | | |
| Ser | Tyr | Val | Gly | Phe | Ser | Val | Val | Tyr | Pro | End | | | | | | 609 |

SEQ ID NO: 4
SEQUENCE TYPE: Amino acids
SEQUENCE LENGTH: 177 amino acids
STRANDEDNESS: Single
TOPOLOGY: Linear
MOLECULE TYPE: Protein
PROPERTIES: fim3 pilinic subunit

| | | | | | | | | | | | | | | | |
|---|---|---|---|---|---|---|---|---|---|---|---|---|---|---|---|
| Asp | Asp | Gly | Thr | Ile | Val | Ile | Thr | Gly | Ser | Ile | Ser | Asp | Gln | Thr | Cys | 16 |
| Val | Ile | Glu | Glu | Pro | Ser | Thr | Leu | Asp | His | Ile | Lys | Val | Val | Gln | Leu | 32 |
| Pro | Lys | Ile | Ser | Lys | Asp | Ala | Leu | Arg | Asp | Asp | Gly | Asp | Thr | Ala | Gly | 48 |
| Ala | Thr | Pro | Phe | Asp | Ile | Lys | Leu | Lys | Glu | Cys | Pro | Leu | Gly | Ala | Leu | 64 |
| Lys | Leu | Tyr | Phe | Glu | Pro | Gly | Ile | Thr | Thr | Asp | Tyr | Asp | Thr | Gly | Asp | 80 |
| Leu | Ile | Ala | Tyr | Lys | Gln | Thr | Tyr | Asp | Ala | Ser | Gly | Asp | Gly | Asp | Leu | 96 |
| Ser | Thr | Val | Ser | Ser | Ala | Thr | Lys | Ala | Lys | Gly | Val | Glu | Phe | Arg | Leu | 112 |
| Ala | Asp | Leu | Asp | Gly | Gln | His | Ile | Arg | Met | Gly | Thr | Asp | Lys | Thr | Thr | 128 |
| Gln | Ala | Ala | Gln | Thr | Phe | Thr | Gly | Lys | Val | Thr | Asp | Gly | Ser | Lys | Ser | 144 |
| Tyr | Thr | Leu | Arg | Tyr | Leu | Ala | Ser | Tyr | Val | Lys | Lys | Pro | Lys | Glu | Asp | 160 |
| Val | Asp | Ala | Ala | Gln | Ile | Thr | Ser | Tyr | Val | Gly | Phe | Ser | Val | Val | Tyr | 176 |
| Pro | | | | | | | | | | | | | | | | 177 |

SEQ ID NO: 5
SEQUENCE TYPE: Nucleotide
SEQUENCE LENGTH: 534 base pairs
STRANDEDNESS: Single -continued
SEQUENCE LISTING TOPOLOGY: Linear
MOLECULE TYPE: genomic DNA
PROPERTIES: fim3 pilinic subunit structural gene

| | | | | | | |
|---|---|---|---|---|---|---|
| AACGACGGCA | CCATCGTCAT | CACCGGCAGC | ATCTCCGACC | AGACCTGCGT | CATCGAAGAG | 60 |
| CCCAGCACCC | TCAACCATAT | CAAGGTCGTG | CAACTGCCCA | AGATTTCCAA | GAACGCGCTC | 120 |
| AGGAACGACG | GCGACACCGC | CGGCGCCACG | CCCTTCGACA | TCAAGCTGAA | GGAATGCCCC | 180 |
| CTGGGCGCGC | TCAAGCTGTA | TTTCGAGCCC | GGCATCACCA | CCAACTACCA | CACGGGCGAT | 240 |
| CTGATTGCCT | ACAAGCAGAC | CTACAACGCA | TCCGGCAACG | GCAACCTGAG | CACCGTGTCG | 300 |
| TCCGCCACCA | AGGCCAAGGG | CGTGGAGTTC | CGCCTGGCCA | ACCTCAACGG | CCAGCACATC | 360 |
| CGCATGGGCA | CGGACAAAAC | CACGCAAGCC | GCGCAAACCT | TTACCGGCAA | GGTCACCAAT | 420 |
| GGCAGCAAGA | GCTACACCCT | GCGCTATCTC | GCCTCGTACG | TGAAGAAACC | CAAGGAAGAT | 480 |
| GCTGACGCGG | CCCAGATCAC | CAGCTACGTC | GGCTTTTCCG | TCGTCTACCC | CTGA | 534 |

SEQ ID NO: 6
SEQUENCE TYPE: Nucleotide
SEQUENCE LENGHT: 609 base pairs
STRANDEDNESS: Single
TOPOLOGY: Linear
MOLECULE TYPE: genomic DNA
FEATURES: from 1 to 75 bp leader sequences;
from 76 to 606 mature peptide
PROPERTIES: fim3 pilinic subunit gene

| | | | | | | |
|---|---|---|---|---|---|---|
| ATGTCCAAGT | TTTCATACCC | TGCCTTGCGC | GCCGCGCTTA | TCCTTGCCGC | CTCGCCCGTA | 60 |
| CTGCCAGCGC | TGGCCAACGA | CGGCACCATC | GTCATCACCG | GCAGCATCTC | CGACCAGACC | 120 |
| TGCGTCATCG | AAGAGCCCAG | CACCCTCAAC | CATATCAAGG | TCGTGCAACT | GCCCAAGATT | 180 |
| TCCAAGAACG | CGCTCAGGAA | CGACGGCGAC | ACCGCCGGCG | CCACGCCCTT | CGACATCAAG | 240 |
| CTGAAGGAAT | GCCCCCTGGG | CGCGCTCAAG | CTGTATTTCG | AGCCCGGCAT | CACCACCAAC | 300 |
| TACGACACGG | GCGATCTGAT | TGCCTACAAG | CAGACCTACA | ACGCATCCGG | CAACGGCAAC | 360 |
| CTGAGCACCG | TGTCGTCCGC | CACCAAGGCC | AAGGGCGTGG | AGTTCCGCCT | GGCCAACCTC | 420 |
| AACGGCCAGC | ACATCCGCAT | GGGCACGGAC | AAAACCACGC | AAGCCGCGCA | AACCTTTACC | 480 |
| GGCAAGGTCA | CCAATGGCAG | CAAGAGCTAC | ACCCTGCGCT | ATCTCGCCTC | GTACGTGAAG | 540 |
| AAACCCAAGG | AAGATGTCGA | CGCGGCCCAG | ATCACCAGCT | ACGTCGGCTT | TTCCGTCGTC | 600 |
| TACCCCTGA | | | | | | 609 |

We claim:

1. An isolated and purified DNA molecule which codes for the mature pilinic subunit fim3 of *Bordetella pertussis* and is represented by the following nucleotide sequence:

```
AACGACGGCA CCATCGTCAT CACCGGCAGC          60
           ATCTCCGACC AGACCTGCGT CATCGAAGAG
CCCAGCACCC TCAACCATAT CAAGGTCGTG         120
           CAACTGCCCA AGATTTCCAA GAACGCGCTC
```

| | | | | | | |
|---|---|---|---|---|---|---|
| AGGAACGACG | GCGACACCGC | CGGCGCCACG | | | | 180 |
| | | CCCTTCGACA | TCAAGCTGAA | GGAATGCCCC | | |
| CTGGGCGCGC | TCAAGCTGTA | TTTCGAGCCC | | | | 240 |
| | | GGCATCACCA | CCAACTACGA | CACGGGCGAT | | |
| CTGATTGCCT | ACAAGCAGAC | CTACAACGCA | | | | 300 |
| | | TCCGGCAACG | GCAACCTGAG | CACCGTGTCG | | |
| TCCGCCACCA | AGGCCAAGGG | CGTGGAGTTC | | | | 360 |
| | | CGCCTGGCCA | ACCTCAACGG | CCAGCACATC | | |
| CGCATGGGCA | CGGACAAAAC | CACGCAAGCC | | | | 420 |
| | | GCGCAAACCT | TTACCGGCAA | GGTCACCAAT | | |
| GGCAGCAAGA | GCTACACCCT | GCGCTATCTC | | | | 480 |
| | | GCCTCGTACG | TGAAGAAACC | CAAGGAAGAT | | |
| GTCGACGCGG | CCCAGATCAC | CAGCTACGTC | | | | 534 |
| | | GGCTTTTCCG | TCGTCTACCC | CTGA | | |

2. A cloning vector for expression in host cells, containing the DNA molecule according to claim 1 wherein the DNA molecule is placed under the control of promoter regulation sequences and a ribosomal recognition site recognized by the host cells.

3. An expression cloning vector according to claim 2 deposited as pSM 306 ATCC 68067.

4. A cell selected from the group consisting of bacterial cells, yeast cells, or mammalian cells transformed by a vector according to claim 2.

5. A cell according to claim 4, wherein the bacterium is selected from the group consisting of Bordetella, *Escherichia coli*, and *Bacillus subtills*.

6. A microorganism according to claim 5 deposited as *Escherichia coli* JM 101 (pSM 306) ATCC 68067.

7. An isolated and purified DNA molecule which codes for a precursor of the pilinic subunit fim3 of *Bordetella pertussis* and is represented by the following nucleotide sequence:

| | | | | | | |
|---|---|---|---|---|---|---|
| ATGTCCAAGT | TTTCATACCC | TGCCTTGCGC | GCCGCGCTTA | TCCTTGCCGC | CTCGCCCGTA | 60 |
| CTGCCAGCGC | TGGCCAACGA | CGGCACCATC | GTCATCACCG | GCAGCATCTC | CGACCAGACC | 120 |
| TGCGTCATCG | AAGAGCCCAG | CACCCTCAAC | CATATCAAGG | TCGTGCAACT | GCCCAAGATT | 180 |
| TCCAAGAACG | CGCTCAGGAA | CGACGGCGAC | ACCGCCGGCG | CCACGCCCTT | CGACATCAAG | 240 |
| CTGAAGGAAT | GCCCCCTGGG | CGCGCTCAAG | CTGTATTTCG | AGCCCGGCAT | CACCACCAAC | 300 |
| TACGACACGG | GCGATCTGAT | TGCCTACAAG | CAGACCTACA | ACGCATCCGG | CAACGGCAAC | 360 |
| CTGAGCACCG | TGTCGTCCGC | CACCAAGGCC | AAGGGCGTGG | AGTTCCGCCT | GGCCAACCTC | 420 |
| AACGGCCAGC | ACATCCGCAT | GGGCACGGAC | AAAACCACGC | AAGCCGCGCA | AACCTTTACC | 480 |
| GGCAAGGTCA | CCAATGGCAG | CAAGAGCTAC | ACCCTGCGCT | ATCTCGCCTC | GTACGTGAAG | 540 |
| AAACCCAAGG | AAGATGTCGA | CGCGGCCCAG | ATCACCAGCT | ACGTCGGCTT | TTCCGTCGTC | 600 |
| TACCCCTGA | | | | | | 609 |

8. An isolated and purified DNA molecule according to claim 6, wherein the precursor of the pilinic subunit has the following amino acid sequence:

| | | | | | | | | | 30 |
|---|---|---|---|---|---|---|---|---|---|
| ATG | TCC | AAG | TTT | TCA | TAC | CCT | GCC | TTG | CGC |
| Met | Ser | Lys | Phe | Ser | Tyr | Pro | Ala | Leu | Arg |
| | | | | | | | | | 60 |
| GCC | GCG | CTT | ATC | CTT | GCC | GCC | TCG | CCC | GTA |
| Ala | Ala | Leu | Ile | Leu | Ala +1 | Ala | Ser | Pro | Val |
| | | | | | | | | | 90 |
| CTG | CCA | GCG | CTG | GCC | AAC | GAC | GGC | ACC | ATC |
| Leu | Pro | Ala | Leu | Ala | Asn | Asp | Gly | Thr | Ile |
| | | | | | | | | | 120 |
| GTC | ATC | ACC | GGC | AGC | ATC | TCC | GAC | CAG | ACC |
| Val | Ile | Thr | Gly | Ser | Ile | Ser | Asp | Gln | Thr |
| | | | | | | | | | 150 |
| TGC | GTC | ATC | GAA | GAG | CCC | AGC | ACC | CTC | AAC |
| Cys | Val | Ile | Glu | Glu | Pro | Ser | Thr | Leu | Asn |
| | | | | | | | | | 180 |
| CAT | ATC | AAG | GTC | GTG | CAA | CTG | CCC | AAG | ATT |
| His | Ile | Lys | Val | Val | Gln | Leu | Pro | Lys | Ile |
| | | | | | | | | | 210 |
| TCC | AAG | AAC | GCG | CTC | AGG | AAC | GAC | GGC | GAC |
| Ser | Lys | Asn | Ala | Leu | Arg | Asn | Asp | Gly | Asp |
| | | | | | | | | | 240 |
| ACC | GCC | GGC | GCC | ACG | CCC | TTC | GAC | ATC | AAG |
| Thr | Ala | Gly | Ala | Thr | Pro | Phe | Asp | Ile | Lys |
| | | | | | | | | | 270 |
| CTG | AAG | GAA | TGC | CCC | CTG | GGC | GCG | CTC | AAG |
| Leu | Lys | Glu | Cys | Pro | Leu | Gly | Ala | Leu | Lys |
| | | | | | | | | | 300 |
| CTG | TAT | TTC | GAG | CCC | GGC | ATC | ACC | ACC | AAC |
| Leu | Tyr | Phe | Glu | Pro | Gly | Ile | Thr | Thr | Asn |
| | | | | | | | | | 330 |
| TAC | GAC | ACG | GGC | GAT | CTG | ATT | GCC | TAC | AAG |
| Tyr | Asp | Thr | Gly | Asp | Leu | Ile | Ala | Tyr | Lys |
| | | | | | | | | | 360 |
| CAG | ACC | TAC | AAC | GCA | TCC | GGC | AAC | GGC | AAC |
| Gln | Thr | Tyr | Asn | Ala | Ser | Gly | Asn | Gly | Asn |
| | | | | | | | | | 390 |
| CTG | AGC | ACC | GTG | TCG | TCC | GCC | ACC | AAG | GCC |
| Leu | Ser | Thr | Val | Ser | Ser | Ala | Thr | Lys | Ala |
| | | | | | | | | | 420 |
| AAG | GGC | GTG | GAG | TTC | CGC | CTG | GCC | AAC | CTC |
| Lys | Gly | Val | Glu | Phe | Arg | Leu | Ala | Asn | Leu |
| | | | | | | | | | 450 |
| AAC | GGC | CAG | CAC | ATC | CGC | ATG | GGC | ACG | GAC |
| Asn | Gly | Gln | His | Ile | Arg | Met | Gly | Thr | Asp |
| | | | | | | | | | 480 |
| AAA | ACC | ACG | CAA | GCC | GCG | CAA | ACC | TTT | ACC |
| Lys | Thr | Thr | Gln | Ala | Ala | Gln | Thr | Phe | Thr |
| | | | | | | | | | 510 |
| GGC | AAG | GTC | ACC | AAT | GGC | AGC | AAG | AGC | TAC |
| Gly | Lys | Val | Thr | Asn | Gly | Ser | Lys | Ser | Tyr |
| | | | | | | | | | 540 |
| ACC | CTG | CGC | TAT | CTC | GCC | TCG | TAC | GTG | AAG |
| Thr | Leu | Arg | Tyr | Leu | Ala | Ser | Tyr | Val | Lys |
| | | | | | | | | | 570 |
| AAA | CCC | AAG | GAA | GAT | GTC | GAC | GCG | GCC | CAG |
| Lys | Pro | Lys | Glu | Asp | Val | Asp | Ala | Ala | Gln |
| | | | | | | | | | 600 |
| ATC | ACC | AGC | TAC | GTC | GGC | TTT | TCC | GTC | GTC |
| Ile | Thr | Ser | Tyr | Val | Gly | Phe | Ser | Val | Val |
| TAC | CCC | TGA | | | | | | | |
| Tyr | Pro | End | | | | | | | |

9. An isolated and purified DNA molecule according to claim 1, which codes for a protein pilinic subunit fim3, wherein the protein has the following amino acid sequence (SEQ. ID. NO. 4):

| Asn | Asp | Gly | Thr | Ile | Val | Ile | Thr | Gly | Ser | Ile | Ser | Asp | Gln | Thr | Cys | 16 |
|---|---|---|---|---|---|---|---|---|---|---|---|---|---|---|---|---|
| Val | Ile | Glu | Glu | Pro | Ser | Thr | Leu | Asn | His | Ile | Lys | Val | Val | Gln | Leu | 32 |
| Pro | Lys | Ile | Ser | Lys | Asn | Ala | Leu | Arg | Asn | Asp | Gly | Asp | Thr | Ala | Gly | 48 |
| Ala | Thr | Pro | Phe | Asp | Ile | Lys | Leu | Lys | Glu | Cys | Pro | Leu | Gly | Ala | Leu | 64 |
| Lys | Leu | Tyr | Phe | Glu | Pro | Gly | Ile | Thr | Thr | Asn | Tyr | Asp | Thr | Gly | Asp | 80 |
| Leu | Ile | Ala | Tyr | Lys | Gln | Thr | Tyr | Asn | Ala | Ser | Gly | Asn | Gly | Asn | Leu | 96 |
| Ser | Thr | Val | Ser | Ser | Ala | Thr | Lys | Ala | Lys | Gly | Val | Glu | Phe | Arg | Leu | 112 |

(SEQ. ID. NO. 4):

| Ala | Asn | Leu | Asn | Gly | Gln | His | Ile | Arg | Met | Gly | Thr | Asp | Lys | Thr | Thr | 128 |
|---|---|---|---|---|---|---|---|---|---|---|---|---|---|---|---|---|
| Gln | Ala | Ala | Gln | Thr | Phe | Thr | Gly | Lys | Val | Thr | Asn | Gly | Ser | Lys | Ser | 144 |
| Tyr | Thr | Leu | Arg | Tyr | Leu | Ala | Ser | Tyr | Val | Lys | Lys | Pro | Lys | Glu | Asp | 160 |
| Val | Asp | Ala | Ala | Gln | Ile | Thr | Ser | Tyr | Val | Gly | Phe | Ser | Val | Val | Tyr | 176 |
| Pro | | | | | | | | | | | | | | | | 177. |

* * * * *